(12) United States Patent
Hayes et al.

(10) Patent No.: US 8,383,336 B2
(45) Date of Patent: Feb. 26, 2013

(54) ANTISENSE FORMULATION

(75) Inventors: Thomas K. Hayes, Coquitlam (CA); Nicole D. Krilla, Belmont, MA (US); Lori Nixon, Fort Collins, CO (US)

(73) Assignee: Oncogenex Technologies Inc., Vancouver (CA)

( * ) Notice: Subject to any disclaimer, the term of this patent is extended or adjusted under 35 U.S.C. 154(b) by 0 days.

(21) Appl. No.: 12/996,143

(22) PCT Filed: Jul. 13, 2009

(86) PCT No.: PCT/US2009/050382
§ 371 (c)(1),
(2), (4) Date: Dec. 3, 2010

(87) PCT Pub. No.: WO2010/009038
PCT Pub. Date: Jan. 21, 2010

(65) Prior Publication Data
US 2011/0098343 A1   Apr. 28, 2011

Related U.S. Application Data

(60) Provisional application No. 61/082,155, filed on Jul. 18, 2008.

(51) Int. Cl.
*C12Q 1/68* (2006.01)

(52) U.S. Cl. ........... 435/6; 435/325; 435/375; 536/24.5; 536/24.1; 536/24.31

(58) Field of Classification Search .................. None
See application file for complete search history.

(56) References Cited

U.S. PATENT DOCUMENTS

| | | | | |
|---|---|---|---|---|
| 5,514,788 | A * | 5/1996 | Bennett et al. | 536/23.1 |
| 6,900,187 | B2 | 5/2005 | Gleave et al. | |
| 7,101,991 | B2 | 9/2006 | Gleave et al. | |
| 2003/0119768 | A1 * | 6/2003 | Madden et al. | 514/44 |
| 2004/0127441 | A1 | 7/2004 | Gleave et al. | |
| 2009/0312399 | A1 * | 12/2009 | Rivory et al. | 514/44 R |

FOREIGN PATENT DOCUMENTS

| | | |
|---|---|---|
| EP | 0618925 | 7/1993 |
| WO | 9313121 | 7/1993 |
| WO | 2007095316 A2 | 8/2007 |

OTHER PUBLICATIONS

Lai, E. et al., Evidence of Lipoplex Dissociation in Liquid Formulations, Journal of Pharmaceutical Sciences, 2002, pp. 1225-1232, vol. 91, No. 5.

* cited by examiner

*Primary Examiner* — Kimberly Chong
(74) *Attorney, Agent, or Firm* — Larson & Anderson, LLC

(57) ABSTRACT

A room temperature stable and minimal aggregate liquid formulation comprises an oligonucleotide comprising Seq ID No. 1: or comprising a variant oligonucleotide in which no more than 3 non-sequential bases are different from Seq. ID NO. 1 and an aqueous carrier comprising a aggregation-preventing compound selected from the group consisting of mono and disaccharides and/or sugar alcohols.

14 Claims, 5 Drawing Sheets

OGX-427 in PBS (original), Expanded RP-HPLC

OGX-427 in PBS (original), RP-HPLC

OGX-427 in Dextrose, Expanded RP-HPLC

OGX-427 in Captisol, Expanded RP-HPLC

OGX-427 in Prototype Formulations (4 weeks)

OGX-427 in Mannitol-Phosphate Buffer (24 Weeks)

OGX-427 in Mannitol-Tris buffer (24 weeks)

OGX-427 in Prototype Formulations (12 weeks)

ANTISENSE FORMULATION

BACKGROUND OF THE INVENTION

1. Field of Invention

The invention relates to a room temperature storage-stable oligonucleotide liquid formulation. More particularly, the invention relates to a stable formulation of a phosphorothioate oligonucleotide designed to bind to Hsp27 mRNA that also minimizes aggregate formation.

2. Description of Related Art

Hsp-27 antisense oligonucleotide (ASO) is designed to bind to Hsp27 mRNA to inhibit the production of human Hsp27 protein. U.S. Pat. No. 7,101,991 describes a variety of Hsp27 ASO.

Early animal study doses of OGX-427, or Hsp27 ASO Seq. Id. No. 1, formulated in a phosphate buffered saline (PBS), in an isotonic solution at the target pH of 7.4, showed good biological effect. However, at higher concentrations of the ASO, the OGX-427 formulations formed non-covalent aggregates after several days under both ambient and refrigerated conditions, and as a result were undesirable for clinical use. A PBS formulation solution had performed satisfactorily for a similar antisense product (see U.S. Pat. No. 6,900,187 relating to a clusterin ASO) and it had been expected that a similar formulation solution could be used for HSP27 ASO. However as explained above and shown below, a PBS solution of HSP27 ASO was not practical as a clinical formulation.

Liquid formulations for injectable administration of ASO drug products have customarily been refrigerated to assure adequate long-term stability. Lyophilization of an oligonucleotide formulation to powder (freeze-drying) with reconstitution just prior to use can be utilized to provide drug product delivery system with adequate stability profiles. However, there are significant commercial benefits to liquid formulations of oligonucleotides, particularly those that remain stable under ambient (room temperature) conditions.

U.S. Patent Publication 2003/0119768 discloses observations regarding a 15-mer antisense sequence targeting c-myc mRNA, namely AACGTTGAGG GGCAT (Seq. ID No. 2). This sequence, which includes four consecutive G residues, was observed to undergo aggregation to formed multimers with increased toxicity. The publication therefore disclosed disruption of the multimers prior to use. One approach disclosed is addition of a saccharide cryoprotectant such as mannitol, sucrose, glucose, trialose or lactose prior to lyophilization. This was found to reduce multimer formation upon reconstitution with water. No information was provided about the long-term solution stability and avoidance of aggregation, however.

An ASO subject to aggregation would be an unfavorable clinical candidate for a company's drug pipeline, regardless of the biological efficacy, and would not be further developed. However, the biological characteristics of Hsp27 ASO in vivo were so favorable that an effort to overcome the problem of aggregation and stability when stored in a liquid formulation for extended time periods was made.

Additionally, it should also be noted that ASO therapeutics remain expensive to manufacture, and that any reduction in their waste or cost of storage would be an added benefit and might make the difference between a commercializable and non-commercializable drug.

SUMMARY OF THE INVENTION

In testing to find a formulation that would provide acceptable solution stability and reduce non-covalent aggregation of ASOs having Seq. ID No. 1, it was found that mannitol (5%) was able to maintain very low aggregation levels at temperatures ranging from −20 degrees C. to 60 degrees C. for period of 24 weeks. A similar result was observed when dextrose was used in place of mannitol. Overall stability was good up to 40 degrees C. for this time period. Thus, the present invention provides a room temperature stable and minimal aggregate drug product liquid formulation comprising an ASO comprising Seq ID No. 1: or comprising a variant oligonucleotide in which no more than 3 non-sequential bases are different for Seq. ID NO. 1 and an aqueous carrier comprising an aggregation-preventing compound selected from among mono and disaccharides such as dextrose and lactose and sugar alcohols such as mannitol and sorbitol. In specific embodiments, the ASO consists of Seq. ID No. 1 or a variant in which no more than 3 non-sequential bases are different for Seq. ID NO. 1. The carrier may also comprise phosphate buffer or Tris buffer.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

In drawings which illustrate embodiments of the invention.

DETAILED DESCRIPTION

Figure 1:
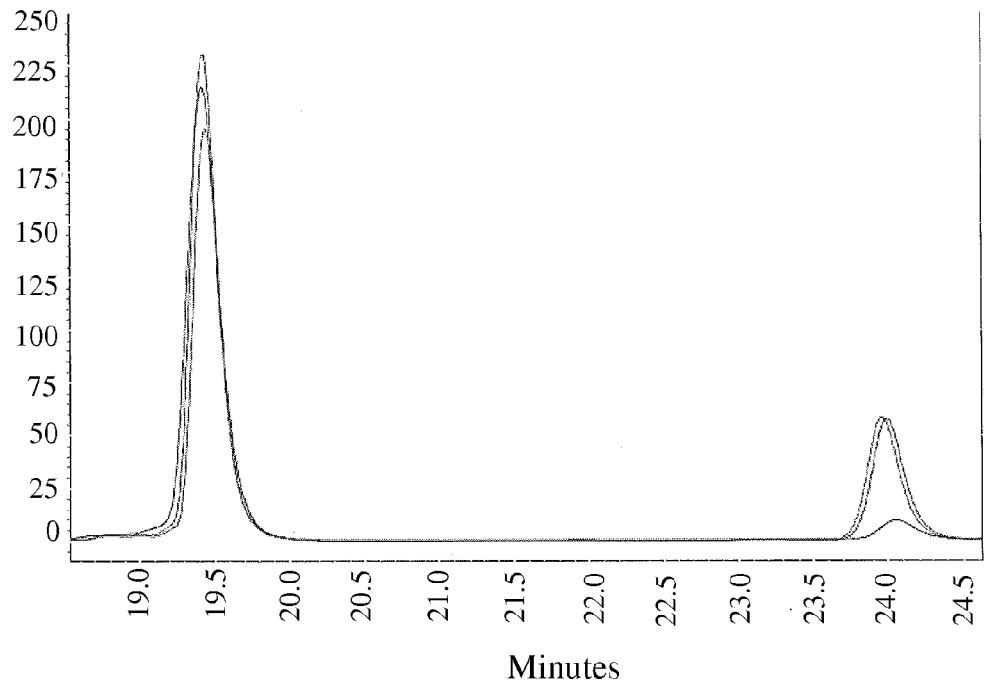
FIG. 1 is an expanded HPLC chromatogram showing two peaks (peak on left is OGX-427 oligonucleotide monomer, and the right peak is aggregate) for OGX-427 in phosphate buffered saline (~70-75 mg/mL) on day 0, 3 and 5 of storage at 40° C. illustrating increase in aggregate over time.
Figure 2:
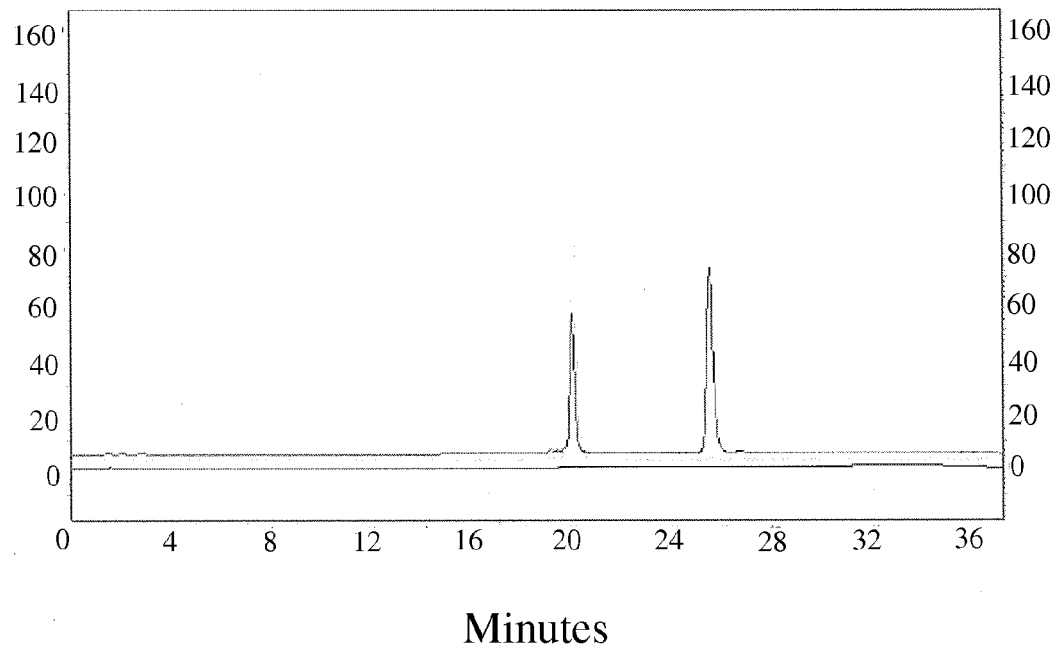
FIG. 2 is an HPLC chromatogram showing OGX-427 oligonucleotide and its aggregate (peak on right). Highly aggregated sample (>50%) was generated from a solution prepared to contain 200 mg/mL OGX-427 in PBS and aged 4 days at ambient conditions prior to analysis.

In typical oligonucleotide compound, phosphate groups covalently link adjacent nucleosides to one another to form a linear polymeric compound. Within the oligonucleotide structure, the phosphate groups are referred to as forming the internucleoside backbone of the oligonucleotide. The normal linkage or backbone of RNA and DNA is a 3' to 5' phosphodiester linkage. OGX-427 is a targeted ASO therapeutic that inhibits expression of heat shock protein 27 (Hsp27). OGX-427 drug substance or active pharmaceutical ingredient (API) is a synthetic oligonucleotide with phosphorothiolated internucleotide linkages commonly classified as 4-12-4 MOE gapmer oligonucleotide (see Isis Pharmaceuticals patent EP 0618925 for discussion of gapmers, incorporated herein by reference, and U.S. Pat. No. 7,101,991 for specific information on OGX-427).

OGX-427 (Hsp27 ASO Seq. Id. No. 1) can be depicted as:

wherein the underlined nucleosides (G, A, $^{Me}C$, and $^{Me}U$) denote 2'-O-methoxyethyl (2'-MOE) modifications of the ribonucleosides guanosine, adenosine, 5-methylcytidine and 5-methyluridine; wherein the G, $^{Me}C$, and T represent the deoxyribonucleosides 2'-deoxyguanosine, 2'-deoxy-5-methylcytidine, and 2'-deoxythymidine; and wherein the internucleotide linkages are phosphorothioate diesters (sodium salts).

The CAS Registry Number (CAS#) for OGX-427 is 915443-09-3 and the CAS Index name is "DNA, d(P-thio) ([2'-O-(2-methoxyethyl)]rG-[2'-O-(2-methoxyethyl)]rG(-{2'-O-(2-methoxyethyl)]rG-[2'-O-(2-methoxyethyl)]rA-m5rC-G-m5rC-G-G-m5rC-G-m5rC-T-m5rC-G-G-2'-O-(2-methoxyethyl)]m5rU-{2'-O-(2-methoxyethyl)]m5rC-[2'-O-(2-methoxyethyl)]rA-[2'-O-(2-methoxyethyl)]m5rU), nonadecasodium salt.

The present invention applies to formulations of OGX-427 and to formulations of antisense therapeutics which are substantially the same as OGX-427. Thus, they consist of Seq. ID No. 1, or the ASO in the formulations of the invention consist of an oligonucleotide variant of this sequence in which no more than 3 non-sequential bases are changed relative Seq. ID No. 1 that retains the ability to inhibit expression of Hsp27. The ASO may also be longer than Seq. ID No. 1 or the above-stated variant through the addition of terminal bases, while remaining an oligonucleotide (less than 100 bases in length) and retaining the ability to inhibit expression of Hsp27. Such longer oligonucleotides are said to comprise Seq. ID No. 1, or an oligonucleotide variant of this sequence in which no more than 3 non-sequential bases are changed relative Seq. ID No. 1.

The particular sequence of OGX-427 suggested that the likelihood of aggregation would be influenced by the number of guanosine ribonucleosides (G) in the oligonucleotide sequence of only 20 There are nine guanosine residues in OGX-427; a number comprising almost 50% of the sequence. Aggregation may be due to strong Watson-Crick complementarity base interaction or to formation of higher-order structures, although it is not applicant's intention to be bound by any particular mechanism for aggregation.

As previously described, the initial choice of formulation for OGX-427 was a PBS solution at pH 7.4. At higher concentrations, an additional peak in the HPLC chromatogram was observed in the solution; this peak was later determined to be a non-covalent aggregate.

Anecdotal historical information suggests antisense compounds having potential for aggregation issues have essentially not been developed, leaving no teaching in the art as to how the problem of aggregation and poor stability could be solved.

Applicants therefore selected potential excipients to accomplish a number of experimental needs: the required solubility and stability of OGX-427 and the compatibility of the OGX-427 product with intravenous (IV) administration.

OGX-427 in PBS acted as a control in monitoring conditions and various types of excipients which were hypothesized to possibly influence aggregation of OGX-427. Disruption of non-covalent aggregate formed in the presence of sodium chloride or other salts could help with enabling a formulation design. Similarly, cyclodextrins can encapsulate drugs, which may prevent the formation of OGX-427 aggregates. Introduction of organic cosolvents may disrupt hydrogen-bonding phenomena which otherwise permits aggregation. Within this category, DMSO was known specifically by OncoGenex to help reverse aggregate formation. Formulations containing simple sugars also could alter hydrogen bonding interactions to inhibit aggregation. Upon screening different type of excipients there was observed significant variation among these formulations in terms of their ability to prevent aggregation of Hsp27 ASO Seq. Id. No. 1 as shown in Table 1.

Although generally sugar/sugar alcohols looked promising experimental efforts focused on narrowed selection as likely representative of these classes of excipients. Further development led to several Prototype Formulations including ones containing mannitol and dextrose that were prepared and studied periodically for up to 24 weeks for aggregate formation and general stability. The results from these studies achieved remarkable evidence of stability for select formulations, even at storage at up 40° C. for several weeks. The results indicate a potential long-term room temperature storage liquid formulation for OGX-427.

Based on the results extrapolating the observations to general antisense oligonucleotides, related compounds ("phosphorthioate oligonucleotides") particularly those with high GC content, for example in excess of 50%, more specifically in excess of 65% could be rendered stable at room temperature in liquid formulations by using mannitol, dextrose or other sugar or sugar alcohol and optionally an appropriate buffer such as phosphate buffer as in the invention.

Such compositions are preferably utilized in a method in which the antisense is formulated in a liquid formulation with the sugar or sugar alcohol, and maintained in the liquid state for a period of time in excess of 6 hours, optionally in excess of 12 hours or 18 hours, after which time the liquid formulation is used as a therapeutic composition.

Materials and Methods

Equipment

HPLC System was Shimadzu LC-10 with UV detection and autosampler; and Delta Pak™ HPLC column (C18 5 μm 300 Å 2.1×150 mm).

Chemicals

Standard buffers, sugars and solvents such as D-mannitol, dextrose, Tris hydroxymethyl aminomethane (Tris), phosphoric acid, monobasic sodium phosphate, dibasic sodium phosphate, tetrabutylammonium hydrogen sulfate, acetonitrile, sorbitol, lactose, sucrose, tartaric acid, Polysorbate 80 polyoxyethylene (20) sorbitan monooleate, phosphate buffer, PEG-300, PEG-400 and dimethyl-acetamide, were obtained from Sigma (St. Louis, Mo.), Aldrich (St. Louis, Mo.), Spectrum Chemicals (Gardena, Calif.), VWR (West Chester, Pa., or J T Baker (Phillipsburg, N.J.).

OGX-427 was manufactured for the applicant by a contract manufacturer.

Polymers such as Cremphor™ EL polyethoxylated castor oil, Poloxamer™ 407 alpha-hydro-omega-hydroxypoly(oxyethylene), a poly(oxypropylene)b poly(oxyethylene) a block copolymer, polyethylene-polypropylene glycol, and propylene glycol were obtained from BASF (Florsham Park, N.J.).

Captisol™, a cyclodextrin, is a product of CyDex (Lenexa, Kans.).

Methods

Hsp27 ASO Seq. Id. No. 1 was prepared as a standard for each occasion of analysis at a concentration in sterile water of 250 µg/mL Hsp27 ASO Seq. Id. No. 1 in a 25 mL volumetric flask. This acted as a starting solution for dilutions of from 25-250 µg/mL to establish for a 5-point linear curve. Each calibration point was injected once into the HPLC.

RP-HPLC Method

Samples generated in the study were analyzed by a reverse-phase (RP)-HPLC method at a column temperature of 50° C., and using a mobile phase "A" of 20 mM tetrabutylammonium hydrogen sulfate and 20 mM Tris base pH 7.8; a mobile phase "B" of acetonitrile; and a mobile phase "C" of water. The flow rate was 0.35 mL/min. Samples were diluted with water to the appropriate concentration, transferred to HPLC vials and held on a cooled autosampler prior to injection. The injection volume was 10 µL and detection was by UV absorption at 260 nm.

Hsp27 ASO stability and aggregate formation was assessed using the HPLC method as described above, and calculated as a percentage of the compound at the regular and aggregated peaks or recorded as concentration mg/mL.

Example 1

Excipient Screening Study

Proponent excipients were selected to accommodate the possibility of a liquid and/or lyophilized formulation for intravenous (IV) administration. The original PBS formulation of OGX-427 acted as a control (~75 mg/mL)

The formulations were aged at 40° C. and at a concentration of 75 mg/mL to simulate "accelerated conditions" based on prior observation of faster aggregation at 40° C. than at ambient temperature and at higher concentrations.

After the 150 mg/mL stock solution was prepared, aliquots were diluted 1:1 with vehicles prepared to twice the target concentration for study. The final solutions contained the target concentration of ~75 mg/mL OGX-427 and excipients. Each sample was prepared in a 1.5 mL tube, which was then closed and briefly vortexed to mix the sample. After preparation, the samples were moved to a 40° C. chamber for the study. All vehicles (except co-solvent based vehicles) were filtered prior to use in the preparation of the OGX-427 solution. All study samples were prepared within approximately 60 minutes of the stock solution being completed.

HPLC Sample Preparation

The OGX-427 solutions were diluted 1000-fold in water to obtain a 750 µg/mL sample for injection on the HPLC.

Figure 3:
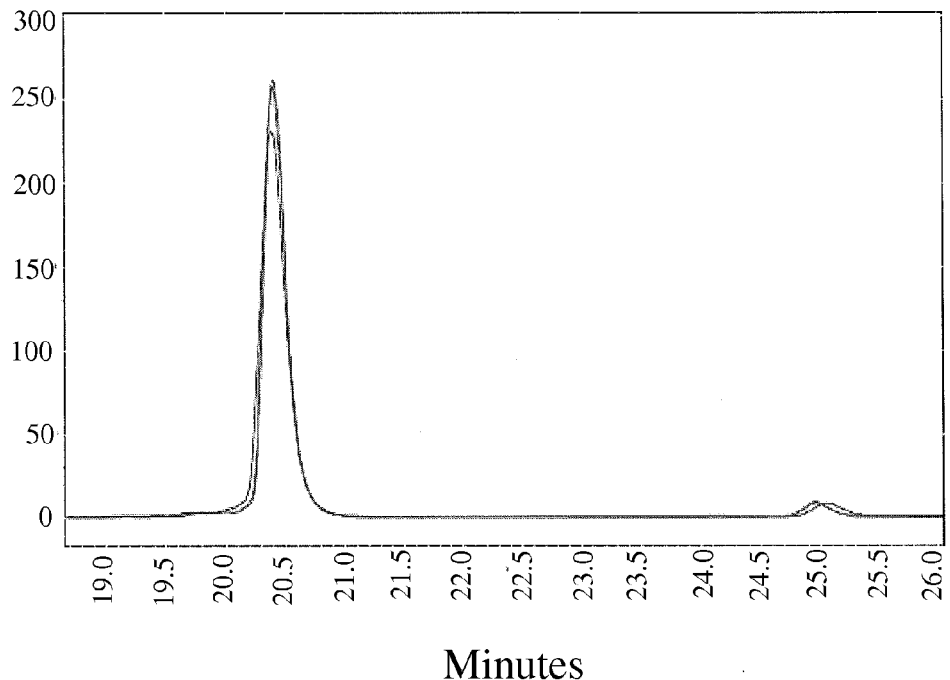
FIG. 3 is an expanded HPLC chromatogram of OGX-427 at 25 mg/mL at 40° C. on day 0, 3 and 5 in a 5% dextrose aqueous formulation without buffer (the 5% mannitol formulation without buffer gave a virtually identical result, see Table 1)
Figure 4:
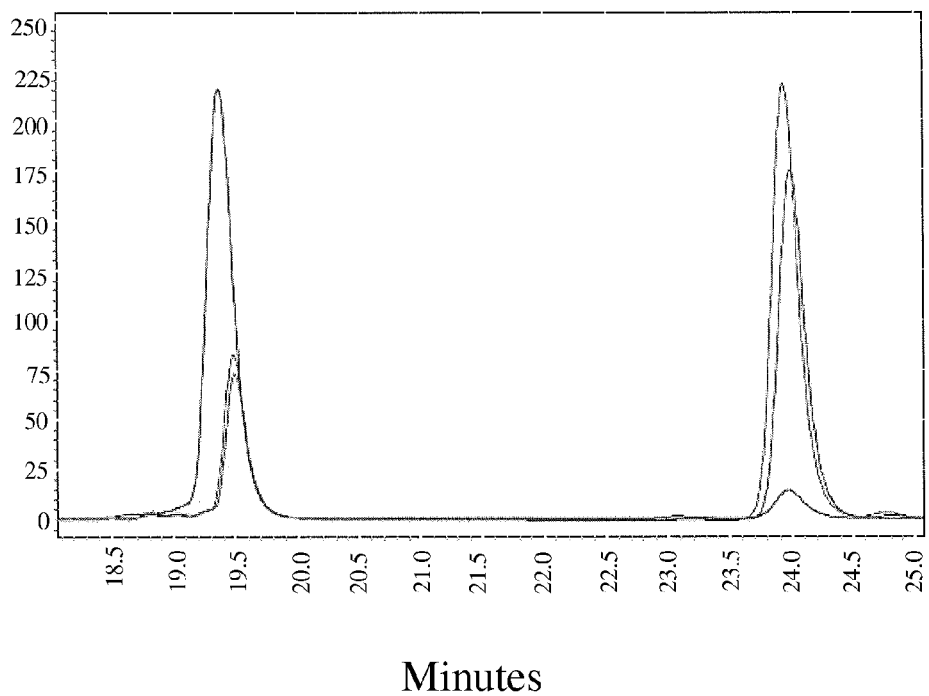
FIG. 4 is an expanded HPLC chromatogram for OGX-427 at 25 mg/mL in a Captisol™ formulation at 40° C. at day 0, 3 and 5; showing increase in aggregate formation.

The information recorded for the samples at preparation (T=0) and five (T=5) days of storage at 40° C. is shown in Table 1. Results for day 3 or T=3 are not shown but follow the same trend as T=5 data. FIGS. 3, 4a and 4b reflect the results for the dextrose, PBS, and 10% Captisol™ formulations.

TABLE 1

Hsp27 ASO Seq. Id. No. 1 (OGX-427) aggregation at time (T) = 0 and 5 days in various excipients, stored 40° C. and 75 mg/mL concentration

| Vehicle | T = 0 ASO, mg/ML | T = 0 Main Area % | T = 0 Aggr Area % | T = 5 ASO, mg/ML | T = 5 Main Area % | T = 5 Aggr Area % |
|---|---|---|---|---|---|---|
| Water | 78.1 | 93.38 | 4.91 | 67.8 | 93.09 | 4.29 |
| PBS (1 of 3) | 75.5 | 93.99 | 4.60 | 52.2 | 71.78 | 25.68 |
| PBS (2 of 3) | 75.4 | 93.48 | 4.66 | 54.2 | 71.87 | 25.63 |
| PBS (3 of 3) | 79.8 | 93.36 | 4.79 | 52.4 | 71.80 | 25.72 |
| 5% Dextrose | 80.0 | 93.43 | 3.86 | 71.3 | 93.64 | 3.83 |
| 5% Mannitol | 80.3 | 92.83 | 4.36 | 68.7 | 93.28 | 4.16 |
| 5% Sorbitol | 76.6 | 93.14 | 4.72 | 73.2 | 93.30 | 4.21 |
| 5% Lactose | 74.9 | 93.00 | 4.44 | 69.8 | 93.28 | 4.23 |
| 5% Sucrose | 79.3 | 92.92 | 4.49 | 71.3 | 93.08 | 4.23 |
| 1 mM Citric Acid | 75.6 | 93.68 | 4.58 | 76.1 | 93.16 | 4.13 |
| 1 mM Tartaric Acid | 80.9 | 94.03 | 4.65 | 72.8 | 93.08 | 4.23 |
| 50 mM Glycine Buffer | 77.7 | 93.63 | 4.61 | 72.1 | 93.18 | 4.18 |
| 50 mM Tris Buffer | 81.8 | 93.50 | 4.70 | 78.6 | 92.59 | 4.74 |
| 50 mM Citrate Buffer | 81.9 | 93.18 | 4.66 | 69.3 | 86.89 | 10.19 |
| 100 mM Phosphate Buffer | 77.5 | 94.15 | 4.61 | 68.4 | 90.29 | 7.18 |
| 15 mM Potassium Chloride | 78.2 | 92.48 | 5.73 | 69.0 | 89.61 | 7.19 |
| 150 mM Potassium Chloride | 72.4 | 89.47 | 5.92 | 62.5 | 82.57 | 13.75 |
| 150 mM Sodium Chloride | 74.1 | 93.44 | 4.76 | 60.6 | 80.38 | 17.19 |
| 5% Poloxamer ™ 407 | 82.3 | 92.85 | 5.42 | 70.7 | 92.00 | 5.51 |
| 10% Polysorbate 80 ™ | 87.7 | 93.32 | 4.86 | 75.4 | 90.38 | 6.34 |
| 10% Propylene Glycol | 75.6 | 93.12 | 5.05 | 72.9 | 90.87 | 6.54 |
| 10% DMSO | 73.1 | 93.37 | 4.91 | 69.4 | 90.68 | 6.79 |
| 10% Dimethylacetamide | 78.6 | 93.21 | 5.10 | 64.9 | 89.40 | 7.97 |
| 10% Cremophor EL ™ | 87.2 | 92.84 | 5.17 | 72.0 | 90.25 | 7.16 |
| 10% PEG-300 | 75.4 | 93.24 | 4.80 | 62.9 | 87.16 | 10.32 |
| 10% PEG-400 | 81.4 | 93.84 | 4.90 | 68.3 | 86.67 | 10.71 |
| 10% Captisol ™ | 79.0 | 92.66 | 5.37 | 35.7 | 46.50 | 50.86 |
| 25% Captisol ™ | 76.4 | 90.87 | 6.83 | 19.9 | 21.60 | 74.66 |

There were distinct differences in the performance of some of the excipients observed within the five day period and under the accelerated test conditions. Some that were notably better than the original PBS formulation at reducing or preventing the amount of OGX-427 aggregation, i.e. maintaining OGX-427 as a monomer, included 5% dextrose and 5% mannitol and related excipients such as sucrose, lactose and sorbitol.

No further testing was done on the organic cosolvents after the initial screen, because their overall behavior did not help prevent aggregate formation, even though they might have been expected to interfere with the hydrogen bonding and subsequent aggregate formation.

Example 2

Liquid Prototype Formulations

Further experiments focusing on dextrose or mannitol, in combinations with either sodium phosphate or Tris buffer or unbuffered, were undertaken.

Five liquid prototype formulations with OGX-427 formulated to 25 mg/mL were studied over temperature and time points: 5% mannitol (V1), 5% mannitol and 10 mM Tris buffer at pH 7.4 (V2), 5% mannitol and 10 mM sodium phosphate buffer at pH 7.4 (V3), 5% dextrose (V4), and 5% dextrose and 10 mM Tris buffer, pH 7.4 (V5).

Figure 5:
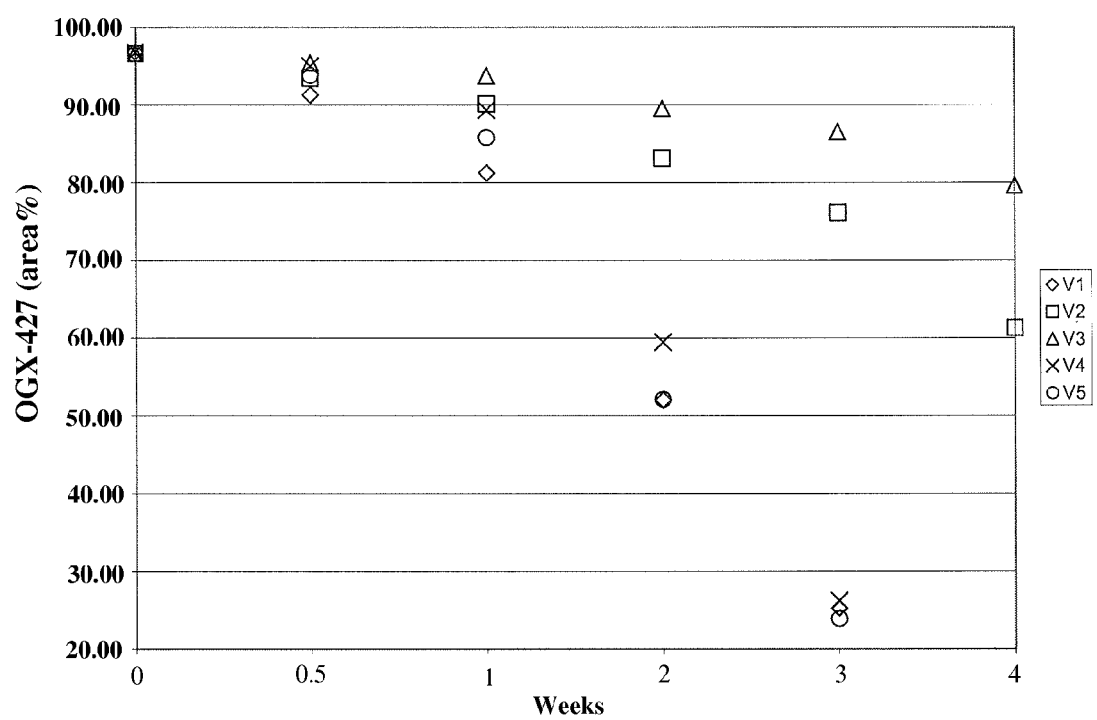
FIG. 5 is a plotted representation of the OGX-427 main peak area % purity (~25 mg/mL) over 4 weeks at a storage temperature of 60° C. for five formulations, namely: 5% mannitol (V1), 5% mannitol in 10 mM Tris buffer at pH 7.4 (V2), 5% mannitol in 10 mM sodium phosphate buffer at pH 7.4 (V3), 5% dextrose (V4), and 5% dextrose in 10 mM Tris buffer, pH 7.4 (V5)
Figure 8:
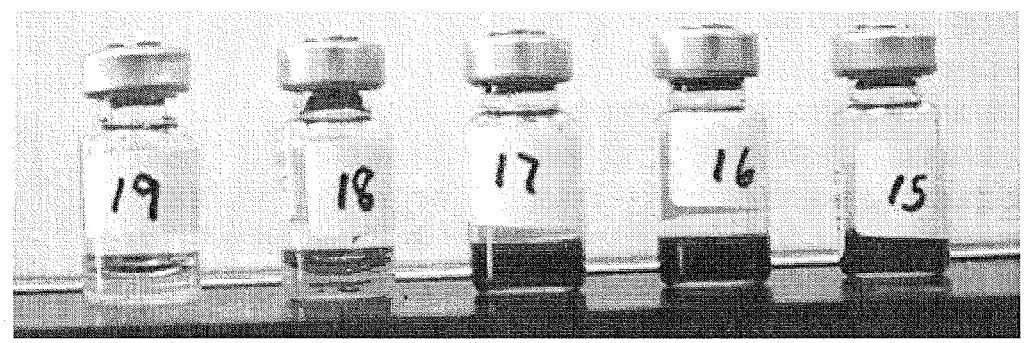
FIG. 8 is a photograph of corresponding stability samples (V1-V5) at the 12 week time point, in glass vials. The effects of generalized degradation of OGX-427 at a concentration of ~25 mg/mL can easily be seen as a darkening of the solution. Vial 19=5% mannitol in 10 mM phosphate buffer or V3; Vial 18=5% mannitol in 10 mM Tris buffer or V2, Vial 17=5% mannitol or V1; Vial 16=5% dextrose in 10 mM Tris buffer or V5; and Vial 15=5% dextrose or V4.

All these prototype solution remained relatively stable based on purity results at −20° C., 5° C., 25° C. and even 40° C. for up to 4 weeks. Likewise, pH and Osmolalilty for the solutions remained stable. All formulations evidenced significant degradation at 60° C. (as shown in FIG. 8); however, Prototypes V1, V4 and V5 did not perform as well (FIG. 5) as V2 and V3; as by the two-week time point, discoloration and particulates could be observed with the naked eye in the formulations stored at 60° C. The data indicated that these three formulations exhibited first-order degradation at the harsher conditions. Thus, although dextrose (buffered or unbuffered) showed some promise in the 5 day aggregation tests, it was inferior to buffered mannitol when stored at very high temperature (60° C.). For the conditions up to twenty four-week time point, these buffered mannitol prototype formulations V2 and V3 appeared clear, colorless, and free of visible particles from all storage conditions. Although some variability was observed in the % aggregate results for V2 (Table 2) and V3 (Table 3) the amount of aggregation observed was maintained at low levels (and may be lower in cases due to reversibility under certain conditions).

TABLE 2

% Aggregate Results for Mannitol-Tris Buffer (24 Weeks)

| Conditions | Weeks | | | | | | | | | |
|---|---|---|---|---|---|---|---|---|---|---|
| | 0 | 0.5 | 1 | 2 | 3 | 4 | 8 | 12 | 16 | 24 |
| −20° C. | 0.71 | — | — | — | — | 0.54 | 0.71 | 0.77 | 0.76 | — |
| 5° C. | 0.71 | — | — | 0.40 | — | 0.50 | 0.65 | 1.29 | 0.63 | 0.05 |
| 25° C. | 0.71 | 0.69 | 0.66 | 0.48 | — | 0.69 | 0.64 | 0.77 | 0.71 | 0.10 |
| 40° C. | 0.71 | 0.68 | 0.60 | 0.39 | — | 0.37 | 0.37 | 0.55 | 0.28 | 0.05 |
| 60° C. | 0.71 | 0.00 | 0.00 | 0.00 | 0.00 | 0.17 | 0.00 | 0.00 | 0.26 | 0.11 |

TABLE 3

% Aggregate Results for Mannitol-Phosphate Buffer (24 Weeks)

| Conditions | Weeks | | | | | | | | | |
|---|---|---|---|---|---|---|---|---|---|---|
| | 0 | 0.5 | 1 | 2 | 3 | 4 | 8 | 12 | 16 | 24 |
| −20° C. | 0.72 | — | — | — | — | 0.58 | 0.68 | 0.86 | 0.78 | — |
| 5° C. | 0.72 | — | — | 0.54 | — | 0.48 | 0.65 | 0.70 | 0.84 | 0.05 |
| 25° C. | 0.72 | 0.73 | 0.65 | 0.48 | — | 0.73 | 0.63 | 0.77 | 0.63 | 0.06 |
| 40° C. | 0.72 | 0.70 | 0.57 | 0.41 | — | 0.38 | 0.45 | 0.56 | 0.31 | 0.05 |
| 60° C. | 0.72 | 0.00 | 0.00 | 0.00 | 0.00 | 0.06 | 0.00 | 0.00 | 0.00 | 0.35 |

The mannitol-phosphate buffered solution, even under accelerated aging conditions (up to 40° C.), provided good stability compared to typical liquid formulations of oligonucleotides that require refrigeration. Another interesting observation was that the Tris buffer did not perform as well as the sodium phosphate buffer (See FIGS. 6 and 7 which show various temperature conditions for a 24 week period for each formulation, and FIG. 5, which shows all five prototypes over a shorter time period (4 weeks).

Figure 6:
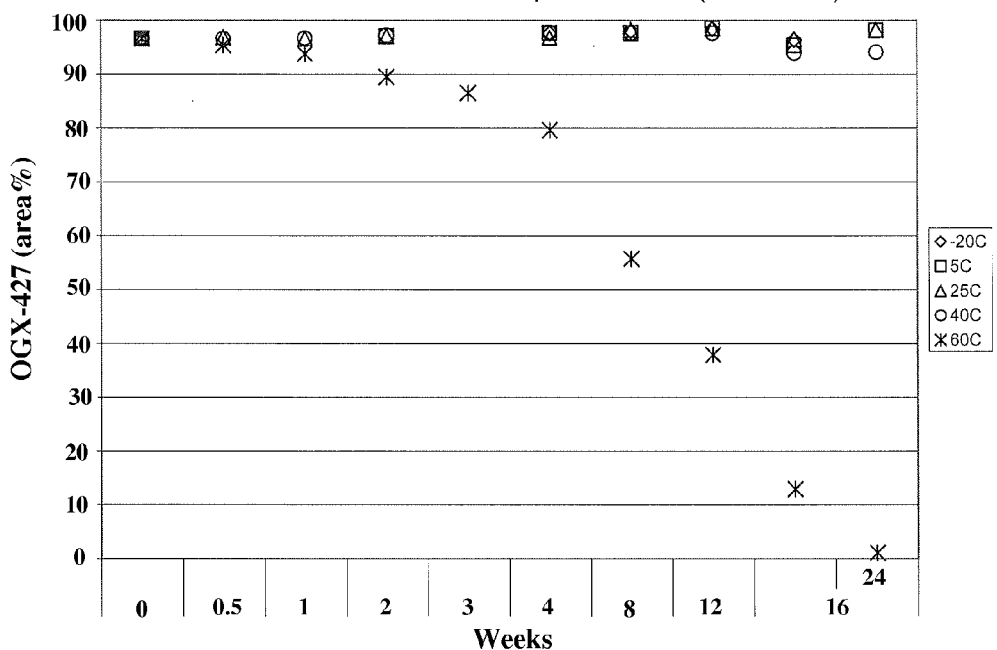
FIG. 6 is a graphical plotted representation of the stability (as exhibited by OGX-427 concentration) of the 5% mannitol and 10 mM sodium phosphate buffer at pH 7.4 formulation (V3) over 24 weeks and at temperatures of −20, 2-8, 25, 40 and 60° C.
Figure 7:
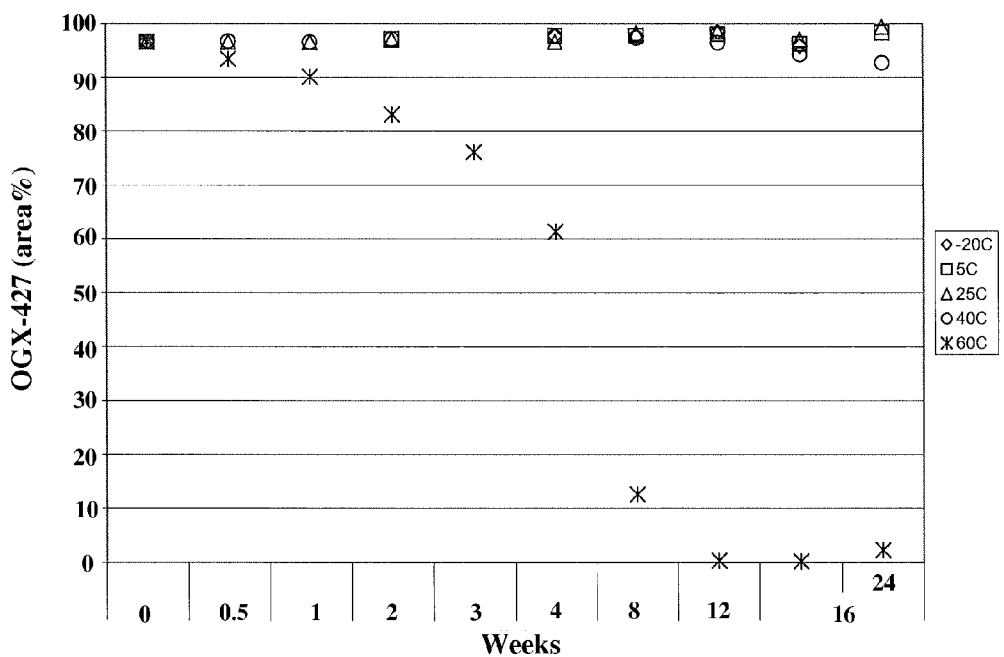
FIG. 7 is a graphical representation of the stability of the 5% mannitol and 10 mM Tris buffer at pH 7.4 formulation (V2) over 24 weeks and at temperatures of −20° C., 2-8° C., 25° C., 40° C. and 60° C.

As shown in FIG. 6, the purity of the V3 formulation (25 mg/mL OGX-427 in 5% mannitol and 10 mM sodium phosphate buffer at pH 7.4) was well conserved throughout the course of the study for storage up to and including 40° C., indicating that the formulation is maintaining the OGX-427 as pure oligonucleotide. A loss in OGX-427 concentration was seen in the formulations stored at 60° C. by the two-week time point. Even at that temperature, however, analysis showed that the loss of purity at 60° C. reflected monomer degradation rather than aggregate formation.

Thus, in some embodiments of formulations of the invention, the ASO is formulated in an aqueous carrier comprising mannitol. The amount of mannitol should be an amount sufficient to provide stability for the desired storage period, for example 1 to 10% by weight. In preferred formulations the carrier is buffered at a biocompatible pH, for example between 7.1 and 7.5. Specific suitable buffers phosphate buffer, pH 7.4 or Tris buffer pH 7.4. These formulations are stable for extended storage periods both under refrigerated conditions and also at room temperature. In other embodiments, in formulations of the invention, the ASO is formulated in an aqueous carrier comprising dextrose. The amount of dextrose should be an amount sufficient to provide stability for the desired storage period, for example 1 to 10% by weight. In preferred formulations the carrier is buffered at a biocompatible pH, for example between 7.1 and 7.5. Specific suitable buffers include phosphate buffer, pH 7.4 or Tris buffer pH 7.4. These formulations are stable as a liquid solution for extended storage periods both under refrigerated conditions and also at room temperature.

The invention claimed is:

1. A method for formulating an antisense oligonucleotide for in vivo injection comprising
   a) obtaining the antisense as a first ingredient, and a sugar or sugar alcohol as a second ingredient, separate from the first ingredient;
   (b) combining the first ingredient and the second ingredient in a liquid aqueous carrier to form a liquid antisense formulation, and maintaining the antisense formulation in the liquid state for a period of time in excess of 6 hours, after which time the liquid formulation is used as a therapeutic composition for in vivo injection.

2. The method of claim 1, wherein the antisense is an oligonucleotide comprising Seq ID No. 1 or a variant oligonucleotide in which no more than 3 non-sequential bases are different from Seq. ID NO. 1 and the sugar or sugar alcohol is selected from the group consisting of mono and disaccharides and/or sugar alcohols.

3. The method of claim 1, wherein the antisense has 65% or more GC content.

4. The method of claim 3, wherein the antisense has 75% or more GC content.

5. The method of claim 2, wherein the carrier further comprises a phosphate buffer.

6. The method of claim 2, wherein the carrier further comprises Tris buffer.

7. The method of claim 6, wherein said antisense oligonucleotide consists of Seq. ID No. 1, or a variant oligonucleotide in which no more than 3 non-sequential bases are different from Seq. ID No. 1.

8. The method of claim 7, wherein the oligonucleotide consists of SEQ ID No. 1 with modifications as follows:

$$5'\text{-}GGGA^{Me}CG^{Me}CGG^{Me}CG^{Me}CT^{Me}CGG^{Me}U^{Me}CA^{Me}U\text{-}3'$$

wherein the italicized nucleosides (G, A, $^{Me}C$, and $^{Me}U$) denote 2'-O-methoxyethyl (2' MOE) modifications of the ribonucleosides guanosine, adenosine, 5-methylcytidine and 5-methyluridine; wherein the G, $^{Me}C$, and T represent the deoxyribonucleosides 2'-deoxyguanosine, 2'-deoxy-5-methylcytidine, and 2'-deoxythymidine; and wherein the internucleotide linkages are phosphorothioate diesters (sodium salts).

9. The method of claim 8, wherein the sugar or sugar alcohol is mannitol.

10. The method of claim 9, wherein the mannitol is present in the aqueous carrier in an amount of 5% by weight.

11. The method of claim 2, wherein the sugar or sugar alcohol is mannitol.

12. The method of claim 2, wherein the mannitol is present in the aqueous carrier in an amount of 5% by weight.

13. A method for administering an antisense oligonucleotide, comprising the steps of:
   (a) obtaining the antisense as a first ingredient and a sugar or sugar alcohol as a second ingredient separate from the first ingredient;
   (b) formulating a liquid composition for in vivo injection by combining the first and second ingredients in a liquid aqueous carrier, and
   (c) using the liquid composition as formulated in treatment of an individual to be treated.

14. The method of claim 13, further comprising the step of storing the composition for a period in excess of 6 hours after the formulating step and before the injecting step.

* * * * *

SEQUENCE LISTING

<160> NUMBER OF SEQ ID NOS: 1

<210> SEQ ID NO 1
<211> LENGTH: 20
<212> TYPE: DNA
<213> ORGANISM: Artificial Sequence
<220> FEATURE:
<223> OTHER INFORMATION: antisense for HSP27

<400> SEQUENCE: 1
gggacgcggc gctcggucau                                            20